United States Patent [19]

Schaus et al.

[11] Patent Number: 4,596,871

[45] Date of Patent: Jun. 24, 1986

[54] PYRAZOLE-RING ALKYLATED PYRAZOLOQUINOLINES

[75] Inventors: John M. Schaus; Diane L. Huser; Richard N. Booher, all of Indianapolis, Ind.

[73] Assignee: Eli Lilly and Company, Indianapolis, Ind.

[21] Appl. No.: 718,761

[22] Filed: Apr. 3, 1985

Related U.S. Application Data

[62] Division of Ser. No. 535,519, Sep. 26, 1983, abandoned.

[51] Int. Cl.[4] ................................. C07D 471/04
[52] U.S. Cl. ........................... 546/82; 546/15; 546/165; 546/166
[58] Field of Search ................................. 546/82

[56] References Cited

U.S. PATENT DOCUMENTS 4,160,093  7/1979  Schwan et al. ................ 546/82

FOREIGN PATENT DOCUMENTS 53119895  10/1978  Japan ................................ 546/82

*Primary Examiner*—Richard A. Schwartz
*Attorney, Agent, or Firm*—Leroy Whitaker; Arthur R. Whale

[57] ABSTRACT

Tautomeric mixtures of trans-($\pm$)-3,5-dialkyloctahydropyrazolo[3,4-g]quinoline, of trans-($\pm$)-6-alkyloctahydropyrazolo[4,3-f]quinoline, and of trans-($\pm$)-1,6-dialkyloctahydropyrazolo[4,3-f]quinoline, individual enantiomer thereof, pharmaceutically-acceptable acid addition salts thereof, and intermediates useful in the preparation thereof, useful as hypotensive agents.

8 Claims, No Drawings

PYRAZOLE-RING ALKYLATED PYRAZOLOQUINOLINES

This application is a division of application Ser. No. 535,519, filed 9/26/83, now abandoned.

BACKGROUND OF THE INVENTION

Tautomeric trans-(±)-5-substituted-7-permissibly-substituted-4,4a,5,6,7,8,8a,9-octahydro-1H(and 2H)-pyrazolo[3,4-g]-quinolines (I and II), active prolactin inhibitors and useful in the treatment of Parkinsonism, are described in Kornfeld and Bach, U.S. Pat. Nos. 4,198,415, 4,230,861 and 4,367,231.

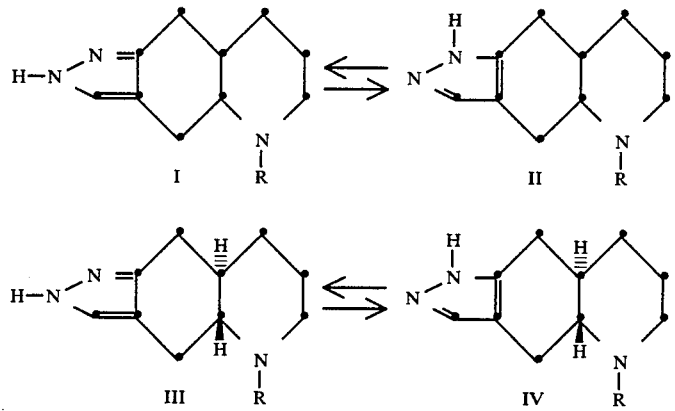

in which R is $C_{1-3}$ alkyl or allyl.

The hypotensive activity of one of the trans-(−)-stereoisomers, 4aR,8aR-5-n-propyl-4,4a,5,6,7,8,8a,9-octahydro-1H(and 2H)-pyrazolo[3,4-g]quinoline (the tautomeric pair III and IV where R is n-propyl) is disclosed by Hahn et al., J. Pharm. Exper. Therap., 206 (1983). Methods for preparing C-3 alkylated octahydro-1H(and 2H)-pyrazolo[3,4-g]quinolines have not been previously known.

The octahydropyrazoloquinolines of the above Kornfeld-Bach patents are prepared according to Reaction Scheme 1.

Reaction Scheme I

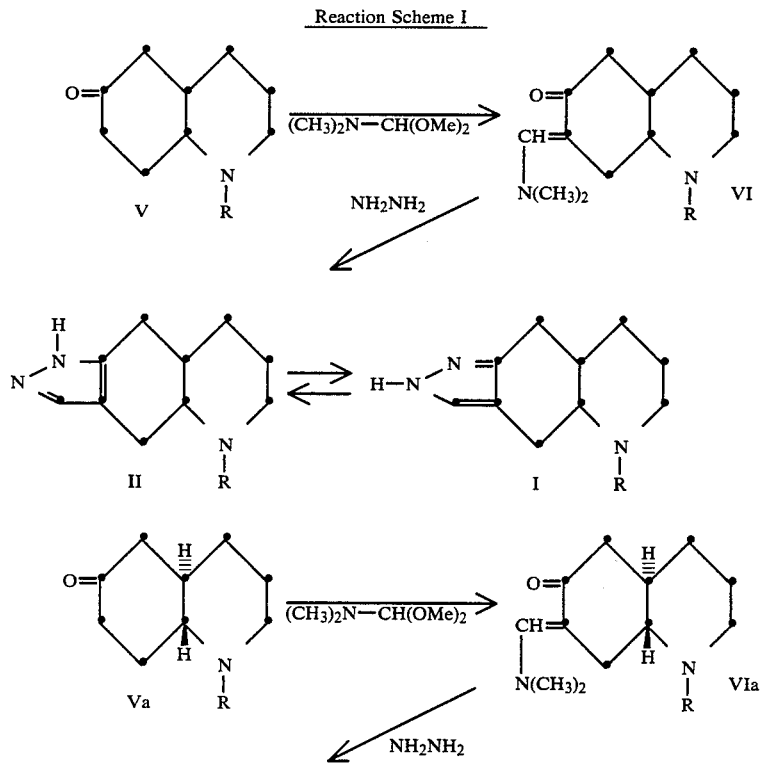

Reaction Scheme I
-continued

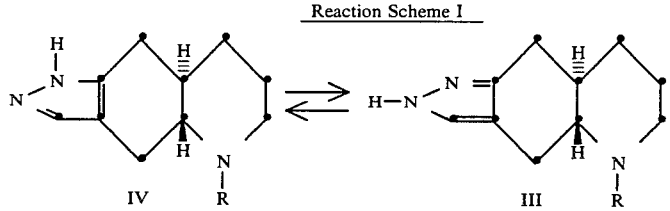

In this Scheme, a trans-(±)-1-alkyl- or allyl-6-oxodecahydroquinoline (V) is condensed with dimethylformamide dimethylacetal to yield (VI) which, on reaction with hydrazine, yields the tautomeric pair (I) and (II).

The copending application of Schaus, Ser. No. 384,817, filed June 3, 1982, provides an alternate method of preparing (V) and the copending application of Schaus and Booher, Ser. No. 439,107, filed Nov. 3, 1982, provides a method of resolving (V) to yield the trans-(−)-(4aR,8aR)stereoisomer (Va), or trans-(+)-stereoisomer, condensation of which with dimethylformamide dimethylacetal yields (VIa) which, on reaction with hydrazine, yields the tautomeric pair (III) and (IV), or the corresponding trans-(+) pair.

Another copending application of Schaus, Ser. No. 438,834, filed Nov. 3, 1982, provides an alternate intermediate, trans-(±), trans-(+) or trans-(−)-7-formyl-1-alkyl-6-oxodecahydroquinoline which, on reaction with hydrazine, yields the tautomeric pairs (I) and (II) or (III) and (IV), and the trans-(+) pair depending on whether the trans-(±)-racemate, the trans-(+) or the trans-(−)-stereoisomer is used as the starting material.

The bicyclic ketones (V) and (Va) are also used as a starting material to prepare a series of octahydro-2H-pyrrolo[3,4-g]quinolines via the intermediates (VI) and (VIa) which are condensed with a glycinate salt (rather than hydrazine) to yield the desired tricyclic compounds—see U.S. Pat. No. 4,311,844 (inventors Bach and Kornfeld), col. 3, Reaction Scheme I. Compounds according to I-IV in which R is allyl and the corresponding pyrroloquinolines are prepared from products in which R is CN or benzyl, by removing the CN or benzyl group and then allylating the resulting secondary amine wherein R is H with an allyl halide.

The prior art cited above does not provide octahydropyrazolo[3,4-g]quinolines having an alkyl substituted in the 3-position of the pyrazole ring, and it is an object of this invention to provide such novel compounds. It is also an object of this invention to provide entirely novel tricyclic compounds and to provide methods for their synthesis.

GENERAL DESCRIPTION OF THE INVENTION

In fulfillment of the above and other objects, this invention provides tautomeric trans-(±)-alkylated octahydropyrazolo[3,4-g] and [4,3-f]quinolines of the structures X, XI, XII and XIII:

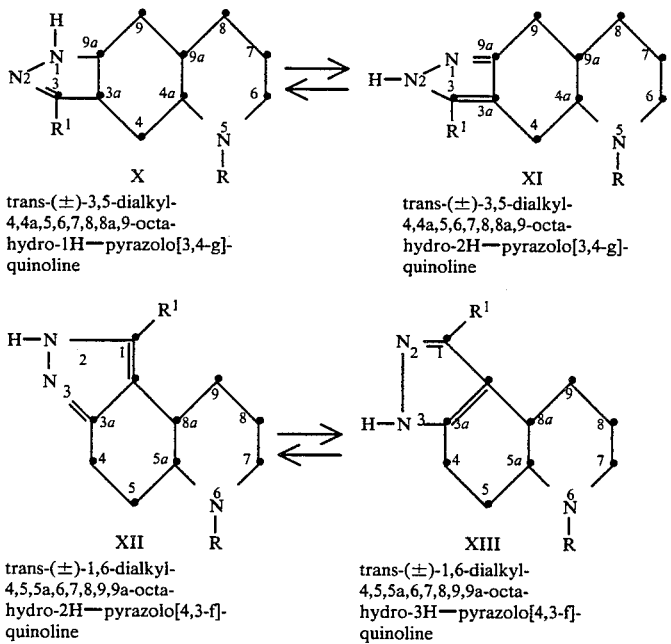

trans-(±)-3,5-dialkyl-4,4a,5,6,7,8,8a,9-octahydro-1H—pyrazolo[3,4-g]-quinoline
X trans-(±)-3,5-dialkyl-4,4a,5,6,7,8,8a,9-octahydro-2H—pyrazolo[3,4-g]-quinoline
XI trans-(±)-1,6-dialkyl-4,5,5a,6,7,8,9,9a-octahydro-2H—pyrazolo[4,3-f]-quinoline
XII trans-(±)-1,6-dialkyl-4,5,5a,6,7,8,9,9a-octahydro-3H—pyrazolo[4,3-f]-quinoline
XIII wherein R is CN, H, $C_1$-$C_3$ alkyl or allyl and $R^1$ is $C_1$-$C_3$ alkyl and pharmaceutically-acceptable acid addition salts thereof.

Structures represented by (X) and (XI) and by (XII) and (XIII) are tautomers; i.e., there is a dynamic equilibrium between each pair of structures shown. When any single member of a tautomeric pair is described, it will be understood that the other tautomer is also described thereby.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, hydroxybutyrate, glycollate, malate, tartrate, methanesulfonate, propanesulfonate, naphthalene-1-sulfonate, naphthalene-2-sulfonate and the like salts.

Compounds represented by the above formulas have two asymmetric centers, at C-4a and C-8a in X and XI and at C-5a and C-9a in XII and XIII. Thus, tautomeric pairs, representing four stereoisomers occurring as two racemates, are indicated by X and XI and by XII and XIII. These racemates are designated as the cis-(±) and trans-(±)-racemates. This invention includes only the latter racemates. The trans-(−)-racemates (4aR,8aR-stereoisomer for X and XI and the 5aR,9aR—stereoisomer for XII and XIII) are designated by the following formulas.

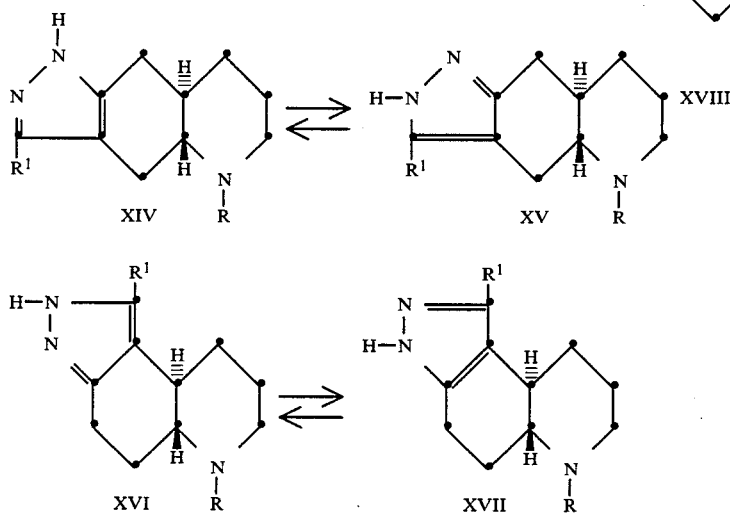

XIV  XV  XVI  XVII

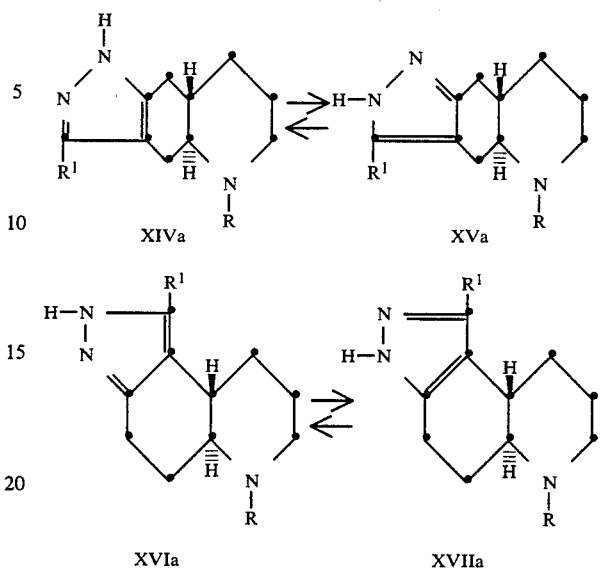

XIVa  XVa  XVIa  XVIIa wherein R and R¹ have their previous meaning.

This invention also provides novel pyrazolo[4,3-f]quinolines of the formulas XVIII and XIX:

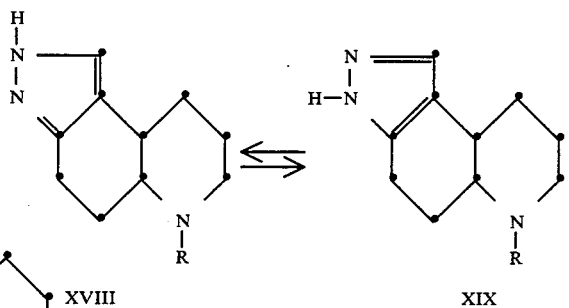

XVIII  XIX wherein R and R¹ have their previous meanings. The trans-(+) enantiomer would have the opposite configuration for the bridgehead hydrogens; i.e., 4aS,8aS for XIVa and XVa and 5aS,9aS for XVIa and XVIIa.

wherein R has its previous meaning (XVIII and XIX correspond to XVI and XVII wherein R¹ is H). The corresponding trans-(−) tautomers have the formulas XX and XXI:

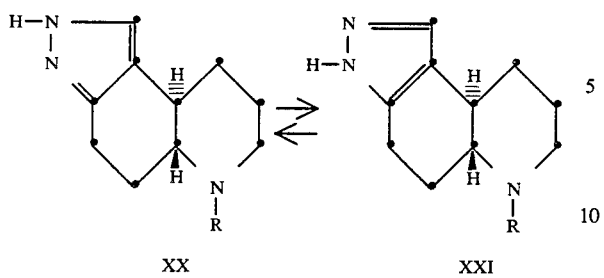

wherein R has its previous meaning. The trans-(+) tautomers have the opposite configuration for the bridgehead hydrogens. Pharmaceutically-acceptable acid addition salts thereof are also part of this invention.

Compounds illustrating the scope of this invention include the following:

Trans-(−)-3,5-dimethyl-4,4a,5,6,7,8,8a,9-octahydro-1H-(and 2H)-pyrazolo[3,4-g]quinoline maleate.

Trans-(−)-1,6-dimethyl-4,5,5a,6,7,8,9,9a-octahydro-2H-(and 3H)-pyrazolo[4,3-f]quinoline tartrate.

Trans-(+)-3-methyl-5-n-propyl-4,4a,5,6,7,8,8a,9-octahydro-1H(and 2H)-pyrazolo[3,4-g]quinoline hydrochloride.

Trans-(−)-1-methyl-6-n-propyl-4,5,5a,6,7,8,9,9a-octahydro-2H-(and 3H)-pyrazolo[4,3-f]quinoline succinate.

Trans-(±)-3-ethyl-5-n-propyl-4,4a,5,6,7,8,8a,9-octahydro-1H(and 2H)-pyrazolo[3,4-g]quinoline sulfate.

Trans-(±)-1-n-propyl-6-methyl-4,5,5a,6,7,8,9,9a-octahydro-2H(and 3H)-pyrazolo[4,3-f]quinoline mesylate.

Trans-(−)-3-methyl-5-allyl-4,4a,5,6,7,8,8a,9-octahydro-1H(and 2H)-pyrazolo[3,4-g]quinoline phosphate.

Trans-(+)-1-ethyl-6-allyl-4,5,5a,6,7,8,9,9a-octahydro-2H(and 3H)-pyrazolo[4,3-f]quinoline tosylate.

Tautomeric pairs, according to X-XI, XII-XIII, XIV-XV, and XVI-XVII, when R is $C_1$-$C_3$ alkyl or allyl and $R^1$ has its previous meaning, are hypotensive agents as are the tautomeric pairs XVIII-XIX and XX-XXI. The corresponding trans-(+) isomeric pairs of tautomers are also useful drugs. In the same tautomeric pairs when R is H or CN, the compounds are predominantly intermediates, useful in preparing the active hypotensive drugs.

The compounds of this invention according to X-XIII are prepared according to Reaction Scheme II below.

Reaction Scheme II

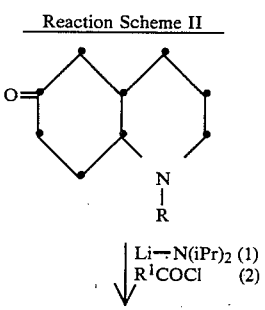

-continued
Reaction Scheme II

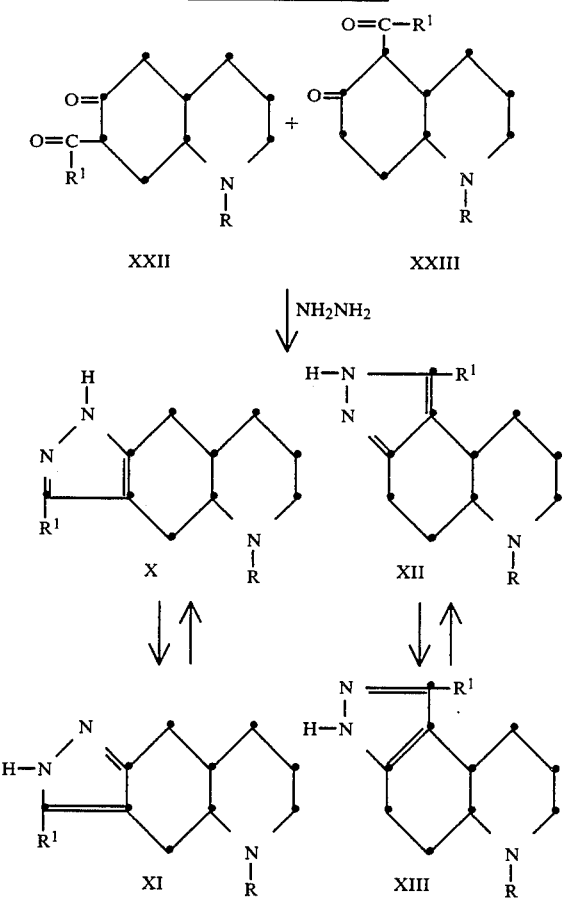

wherein R is $C_1$-$C_3$ alkyl or CN and $R^1$ is $C_1$-$C_3$ alkyl. All formulas represent the trans-(±)-racemate. The trans-(−)-enantiomer as well as the trans-(+)-enantiomer (Va) provided by the method of Schaus and Booher, Ser. No. 439,107, filed Nov. 3, 1982, undergoes identical reactions to provide intermediates of the structures:

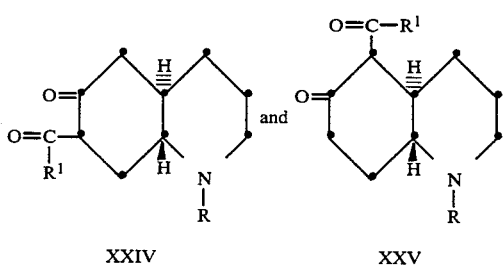

and the trans-(+) derivatives.

These pairs of products such as XXII and XXIII or XXIV and XXV can be separated into the individual isomers by chromatography. However, we prefer to carry out the cyclization reaction with hydrazine on the mixture of acylated 6-oxodecahydroquinolines to yield a mixture of pyrazoles and then to separate the resulting tautomeric pairs by chromatography.

An alternate method exists for preparing the tautomeric pairs XII and XIII or XVI and XVII free from the position isomers X and XI or XIV and XV respectively. This procedure is outlined in Reaction Scheme III below.

Reaction Scheme III

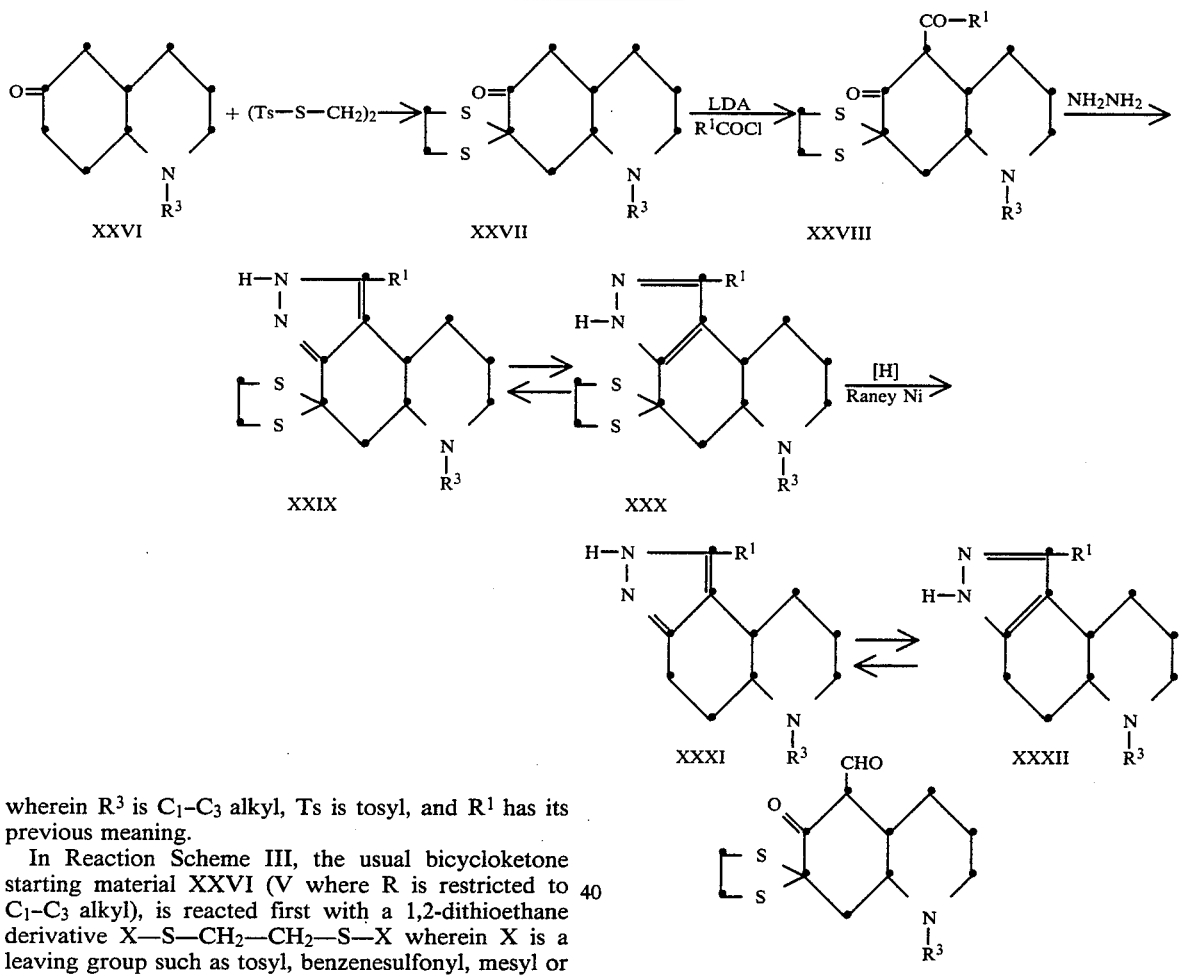

wherein $R^3$ is $C_1$–$C_3$ alkyl, Ts is tosyl, and $R^1$ has its previous meaning.

In Reaction Scheme III, the usual bicycloketone starting material XXVI (V where R is restricted to $C_1$–$C_3$ alkyl), is reacted first with a 1,2-dithioethane derivative X—S—CH$_2$—CH$_2$—S—X wherein X is a leaving group such as tosyl, benzenesulfonyl, mesyl or the like in the presence of pyrrolidine and triethylamine to form a dithioketal at C-7 as a blocking group. The C-5 position is then acylated as before with a lower alkyl halide and lithium diisopropyl amide. Cyclization with hydrazine produces the angular octahydropyrazolo[4,3-f]quinoline tautomeric pair (XXIX and XXX) still carrying the thioketal blocking group, which group is readily removed as by treatment with Raney nickel.

Tautomers of structures XVIII–XIX and XX–XXI are prepared by formylating the blocked ketone XXVIII at C-5, employing any of the prior art formylating procedures, for example ethylformate and base. The reactive intermediate XXXIII is

XXXIII

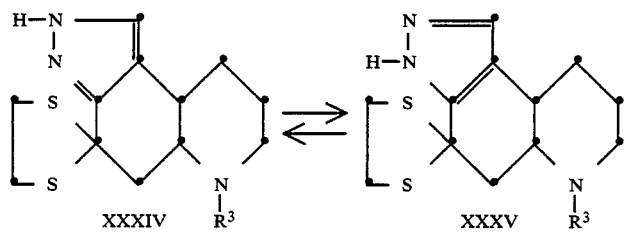

reacted with hydrazine to yield the product XXXIV–XXXV still containing the blocking group.

The blocking group is readily removed, as before, with Raney Ni to yield the pair XVIII–XIX.

The above chemistry is equally adaptable to the preparation of the optically active tautomers XX–XXI by starting with an optically-active starting material XXXVI or its trans-(+) enantiomer.

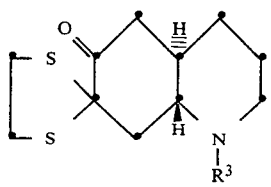

If it is desired to have a 6-allyl group in a final octahydropyrazolo[4,3-f]quinoline prepared by this procedure, the compound is prepared by removing the alkyl group $R^3$ from the final tautomeric mixture, as with CNBr, thus forming a compound according to XII–XIII above in which R is CN. Removal of the cyano group yields a derivative wherein R is H, and this secondary amine is readily allylated, as with allyl chloride, to yield the desired derivative.

Tautomeric pairs according to X and XI wherein R is allyl are prepared via a derivative in which R is CN or H. These derivatives are prepared from the corresponding compound in which R is $C_1$–$C_3$ alkyl by reaction with CNBr, and the resulting N-cyano derivative converted to the secondary amine. The resulting secondary amine can be allylated with an allyl halide to produce the desired N-allyl compound.

Those intermediates in which R is H can also be alkylated with a different alkyl group or alkylated with the same alkyl group containing a tagged (radio-active or isotopic) atom to yield useful products.

This invention is further illustrated by the following specific examples.

EXAMPLE 1

Preparation of trans-(±)-3-methyl-5-n-propyl-4,4a,5,6,7,-8,8a,9-octahydro-1H(and 2H)-pyrazolo[3,4-g]quinoline A 0.5M lithium diisopropylamine solution was prepared by adding 62.5 ml. of n-butyl lithium (1.6 molar in hexane) to 14 ml. of diisopropylamine in 100 ml. of THF at 0° C. After the preparation had been completed, the reagent was diluted to 200 ml. giving a 0.5 molar lithium diisopropylamine solution in tetrahydrofuran/hexane solvent mixture. Twenty-two ml. of this solution was placed in a dry 50 ml. round-bottom flask and the solution cooled to about −78° C. One and ninety-five hundredths grams of trans-(±)-1-n-propyl-6-oxo-decahydroquinoline in 5 ml. of THF were added to the solution and the resulting mixture stirred at about −78° C. for 30 minutes. Next, 1.06 ml. of acetylchloride were added and the reaction mixture was allowed to warm to room temperature. The reaction mixture was stirred for two hours at room temperature and was then poured into water. The alkaline aqueous mixture was extracted several times with equal volumes of methylenedichloride. The methylenedichloride extracts were combined and dried and the methylenedichloride removed to yield 2.895 g. of an orange oil comprising trans-(±)-1-n-propyl-6-oxo-7-acetyldecahydroquinoline formed in the above reaction. The product was purified by chromatography over silica using 4% methanol and methylenedichloride plus ammonia as the original eluant. The percent of methanol was raised to 7.5% and fractions containing trans-(±)-1-n-propyl-6-oxo-5-acetyldecahydroquinoline were combined to yield after evaporation of the solvent 728 mg. of a yellow liquid. NMR indicated that these fractions were mixtures of the two products, trans-(±)-1-n-propyl-6-oxo-7-acetyldecahydroquinoline and trans-(±)-1-n-propyl-5-acetyl-6-oxodecahydroquinoline. The mixture was dissolved in 20 ml. of methanol to which was added 2 ml. of hydrazine and sufficient 15% aqueous hydrochloric acid to adjust the pH to about 9. The reaction mixture was stirred at room temperature for about one hour and then poured into dilute aqueous sodium hydroxide. The alkali insoluble materials were extracted in methylenedichloride. The methylenedichloride extract was dried and the solvent removed therefrom to yield 959 mg. of a yellow oil which was purified by chromatography over silica using 2:1 THF/hexane solvent mixture containing also aqueous ammonium hydroxide. Fractions shown by TLC to contain trans-(±)-3-methyl-5-n-propyl-4,4a,5,6,7,8,8a,9-octahydro-1H(and 2H)-pyrazolo[3,4-g]quinoline were combined to yield 406 mg. of a light yellow oil. The product had the following physical characteristics:

Ultraviolet spectrum: 220 ($\epsilon$=5200).

Infrared spectrum ($CHCl_3$): 3464 cm$^{-1}$; mass spectrum: 233, 204, 125, 124, 96 and 42.

The hydrochloride salt was formed by dissolving the yellow oil in methylenedichloride/ether solvent mixture and saturating with anhydrous gaseous hydrogen chloride. The resulting white solid consisting of trans-(±)-3-methyl-5-n-propyl-4,4a,5,6,7,8,8a,9-octahydro-1H(and 2H)-pyrazolo[3,4-g]quinoline dihydrochloride was separated by filtration. Recrystallization from methanol yielded trans-(±)-3-methyl-5-n-propyl-4,4a,5,6,7,8,8a,9-octahydro-1H(and 2H)-pyrazolo[3,4-g]-quinoline dihydrochloride as fine white needles melting about 250° C.

Analysis Calculated: C, 54.90; H, 8.23; N, 13.72; Cl, 23.15, Found: C, 54.76; H, 8.36; N, 13.72; Cl, 23.37.

(Addendum to Example 1)

The above preparation was repeated using 3.9 g. of trans-(±)-1-n-propyl-6-oxo-decahydroquinoline starting material and about 88 ml. of 0.5M lithium diisopropylamine in THF solution. In this preparation, the LDA solution and starting material were combined at 0° C. after which time the temperature was reduced to −78° C. and the acetyl chloride added thereto. The reactions were worked up and the mixture products isolated as in Example 1. Five and one tenths grams of this mixture was reacted with 5 ml. of hydrazine in 25 ml. of methanol as in Example 1 to yield a mixture of the [4,3-f] and [3,4-g] isomeric pyrazolo quinolines. Chromatographic separation yielded 0.8 g. of trans-(±)-1-methyl-6-n-propyl-4,5,5a,6,7,8,9,9a-octahydro-2H(and 3H)-pyrazolo[4,3-f]quinoline and 1.8 g. of trans-(±)-3-methyl-5-n-propyl-4,4a,5,6,7,8,8a,9-octahydro-1H(and 2H)-pyrazolo[3,4-g]quinoline. Trans-(±)-1-methyl-6-n-propyl-4,5,5a,6,7,8,9,9a-octahydro-2H(and 3H)-pyrazolo[4,3-f]quinoline had the following physical characteristics:

Dihydrochloride salt m.p. 249°–250° C.

Analysis Calculated: C, 54.90; H, 8.23; N, 13.72; Cl, 23.15, Found: C, 54.87; H, 8.08; N, 13.52; Cl, 23.36.

Infrared spectrum ($CHCl_3$): 3462, 3210, 2947, 1448; mass spectrum: 233 (molecular ion), 204, 96, 42; proton nmr ($CDCl_3$): 9.80 (bs, 1H); 3.02 (bd, J=13.5, 1H); 2.30 (s, 3H); 2.06–2.94 (m, 9H); 1.04–1.90 (m, 7H).

EXAMPLE 2

Preparation of trans-(±)-3,5-di-n-propyl-4,4a,5,6,7,8,-8a,9-octahydro-1H(and 2H)-pyrazolo[3,4-g]quinoline and trans-(±)-1,6-di-n-propyl-4,5,5a,6,7,8,9,9a-2H(and 3H)-pyrazolo[4,3-f]quinoline Following the procedure of Example 1, 3.9 g. of trans-(±)-1-n-propyl-6-oxo-decahydroquinoline and about 44 ml. of 0.5 molar lithium diisopropylamine reagent were combined at −78° C. in THF. Three and one tenth ml. of butyryl chloride were added. Six and four tenths grams of a mixture of trans-(±)-1-n-propyl-6-oxo-7-butyryldecahydroquinoline and trans-(±)-1-n-propyl-5-butyryl-6-oxodecahydroquinoline were obtained which were used directly in the next step.

Six and four tenths grams of the above mixture were dissolved in 20 ml. of methanol to which was added 4 ml. of hydrazine. The reaction was carried out and the product isolated as in the previous example. The methylenedichloride extract yielded 6.9 g. of a two spot material comprising trans-(±)-3,5-di-n-propyl-4,4a,5,6,7,8,8a,9-octahydro-1H(and 2H)-pyrazolo[3,4-g]quinoline and the isomeric trans-(±)-1,6-di-n-propyl-4,5,5a,6,7,8,9,9a-octahydro-2H(and 3H)pyrazolo[4,3-f]quinoline which mixture was separated by chromatography over silica into its component compounds using the same eluant as in the previous example. Trans-(±)-3,5-di-n-propyl-4,4a,5,6,7,8,8a,9-octahydro-1H(and 2H)-pyrazolo-[3,4-g]quinoline free base thus prepared was converted by standard procedures to the dihydrobromide salt which melted at 295°-296° C. after recrystallization from a methanol/ethyl acetate solvent mixture.

Analysis Calculated: C, 45.41; H, 6.91; N, 9.93; Br, 37.76, Found: C, 45.52; H, 6.72; N, 9.66; Br, 37.97.

The other chromatographic product, trans-(±)-1,6-di-n-propyl-4,5,5a,6,7,8,9,9a-octahydro-2H(and 3H)-pyrazolo[4,3-f]quinoline, was converted to the dihydrochloride salt having the following analysis:

Analysis Calculated: C, 57.48; H, b 8.74; N, 12.57; Cl, 21.21, Found: C, 57.61; H, 9.02; N, 12.32; Cl, 21.25.

Physical characteristics of 3,4-g isomer: infrared spectrum (CHCl$_3$): 3463, 3210, 2917, 1462.

Mass spectrum: 261 (molecular ion), 223, 125, 96, 41; nmr (CDCl$_3$): 9.7 (bs, 1H); 2.86–3.10 (m, 2H); 2.64–2.86 (m, 2H); 2.38–2.64 (m, 3H); 2.12–2.38 (m, 4H); 1.91 (bd, J=13, 1H); 1.34–1.82 (m, 7H); 1.02–1.30 (m, 1H); 0.97 (t, J=8.1, 3H); 0.91 (t, J=8.1 3H).

Physical chemistry of the 4,3-f isomer was as follows: infrared spectrum (CHCl$_3$): 3461, 3210, 2947, 1457.

Mass spectrum: 261 (molecular ion), 232, 189, 125, 96, 41.

nmr (CDCl$_3$): 9.40 (bs, 1H); 3.04 (bd, J=13, 1H); 2.12–2.86 (m, 11H); 1.34–1.90 (m, 7H); 1.16–1.34 (m, 1H); 0.98 (t, J=8.1, 3H); 0.90 (t, J=8.1, 3H).

EXAMPLE 3

Preparation of trans-(±)-3-ethyl-5-n-propyl-4,4a,5,6,7,8,8a,9-octahydro-1H(and 2H)-pyrazolo[3,4-g]quinoline and trans-(±)-1-ethyl-6-n-propyl-4,5,5a,6,7,8,9,9a-octahydro-2H(and 3H)-pyrazolo[4,3-f]quinoline Following the procedure of Example 1, about 44 ml. of a 0.5M lithium diisopropylamine solution were cooled to −78° C. Three and nine tenths grams of trans-(±)-1-n-propyl-6-oxo-decaquinoline in THF were added and the reaction stirred at −78° C. for 30 minutes. Two and six tenths ml. of propionyl chloride were then added and the reaction mixture warmed to room temperature and stirred overnight at that temperature. The reaction was worked up and the product isolated with the procedure of Example 1. About 4.2 g. of a mixture containing trans-(±)-1-n-propyl-6-oxo-7-propionyldecahydroquinoline and the 5-propionyl isomer were obtained. The mixture caused to react with hydrazine in methanol without further purification to yield a mixture of the two pyrazole isomers. These isomers were separated by chromatography over silica gel using the same solvent system as previously. Trans-(±)-3-ethyl-5-n-propyl-4,4a,5,6,7,8,8a,9-octahydro-1H(and 2H)-pyrazolo[3,4-g]quinoline thus prepared was converted to both the dihydrobromide and dihydrochloride salts.

Analysis Calculated for the dihydrochloride salt: C, 56.25; H, 8.50; N, 13.12; Cl, 22.14, Found: C,56.01; H, 8.72; N, 12.85; Cl, 22.03.

Melting point=271°-275° C. after recrystallization from methanol/ethyl acetate; infrared spectrum (CHCl$_3$): 3464, 3210, 2951, 1625, 1461;

Mass spectrum: 247 (molecular ion), 218, 125, 96, 41; proton nmr (CDCl$_3$): 9.92 (bs, 1H); 2.84–3.10 (m, 2H); 2.68–2.84 (m, 2H); 2.44–2.60 (m, 2H); 2.61 (q, J=8.1, 2H); 2.14–2.32 (m, 4H); 1.91 (bd, J=13, 1H); 1.62–1.82 (m, 3H); 1.44–1.62 (m, 2H); 1.24 (t, J=7.6, 3H); 0.91 (t, J=8.1, 3H).

The dihydrobromide salt of the isomeric material trans-(±)-1-ethyl-6-n-propyl-4,5,5a,6,7,8,9,9a-octahydro-2H(and 3H)-pyrazolo[4,3-f]quinoline (separated by the above chromatographic procedure) melted at 289° C.

Analysis Calculated: C, 44.03; H, 6.65; N, 10.27; Br, 39.05 Found: C, 43.97; H, 6.70; N, 9.99; Br, 39.29.

Infrared spectrum (CHCl$_3$): 3462, 3210, 2952, 1471;

Mass spectrum peaks at 247: (molecular ion), 218, 175, 125, 84; proton nmr (CDCl$_3$): 9.76 (bs, 1H), 3.03 bd, J=12, 1H); 2.12–2.94 (m, 11H); 1.36–1.90 (m, 5H); 1.22 (t, J=8.1, 3H); 1.10–1.36 (m, 1H); 0.90 (t, J=8.1, 3H).

EXAMPLE 4

Preparation of trans-(±)-6-n-propyl-4,5,5a,6,7,8,9,9a-octahydro-2H(and 3H)-pyrazolo[4,3-f]quinoline A reaction mixture was prepared from 1 g. of trans-(±)-1-n-propyl-6-oxodecahydroquinoline and 0.355 g. of pyrrolidine (0.43 ml.) in 50 ml. of acetonitrile. A 4A molecular sieve was added and the reaction mixture stirred under a nitrogen atmosphere at reflux temperature for about three hours. The reaction mixture was then cooled to room temperature and 2 ml. of triethylamine were added followed by 2 g. of 1,2-ditosylthioethane. The resulting reaction mixture was heated to reflux temperature overnight with stirring under a nitrogen blanket. After cooling to room temperature, the reaction mixture was filtered and the solvent removed from the filtrate by evaporation in vacuo. Fifty ml. of 0.1N aqueous hydrochloric acid were added and the new mixture warmed to about 100° for about 30 minutes. The reaction mixture was then cooled to room temperature and the acidic layer extracted with methylenedichloride to remove any acid insoluble material. The acidic layer was then made alkaline with an excess of 14N aqueous ammonium hydroxide. The basic mixture was extracted twice with equal volumes of methylenedichloride. The methylenedichloride extracts were combined. The combined extracts were washed with saturated aqueous sodium chloride and were then dried. Removal of the solvent in vacuo yielded 0.8 g. of a solid comprising trans-(±)-1-n-propyl-6-oxo-7-spiro-1′,3′-dithiolanodecahydroquinoline formed in the above reaction. The compound was purified by chromatography over florisil using 1% methanol in chloroform as the eluant. Fractions containing the desired material were combined to yield 0.5 g. of trans-(±)-1-n-propyl-6-oxo-7-spiro-1′,3-dithiolanodecahydroquinoline having the following physical characteristics:

Melting point (after recrystallization from an hexane/ethyl acetate solvent mixture)=112°-113° C.

Analysis Calculated: C, 58.90; H, 8.12; N, 4.91; S, 22.46, Found: C, 59.12; H, 8.03; N, 4.92; S, 22.36.

A reaction mixture containing 0.9 g. of trans-(±)-1-n-propyl-6-oxo-7-spiro-1′,3′-dithiolanodecahydroquinoline and 2.5 g. of tris(dimethylamino)methane in 30 ml. of toluene were refluxed with stirring for about 4 hours, at which time TLC indicated starting material was no longer present. Volatile constituents were removed in vacuo. The residual oil was dissolved in 50 ml. of methanol and 1 ml. of anhydrous hydrazine was added. This new reaction mixture was stirred overnight at ambient temperature under $N_2$ blanket. Volatile constituents were again removed in vacuo to yield a reddish oil which was purified by chromatography over florisil using 2% MeOH in $CHCl_3$ as the eluant. Fractions containing trans-(±)-4-spiro-1′,3′-thiolano-6-n-propyl-4,5,5a,6,7,8,9,9a-octahydro-2H(and 3H)-pyrazolo[4,3-f]quinoline formed in the above reaction were pooled and the solvents removed in vacuo. A methanol solution of the residue was treated with 22 ml. of 0.1N aqueous hydrochloric acid, (one equivalent) thus forming the hydrochloride salt. Recrystallization of the salt from methanol/ethyl acetate gave 0.9 g. of trans-(±)-6-n-propyl-4-spiro-1′,3′-thiolano-4,5,5a,6,7,8,9,9a-octahydro-2H(and 3H)-pyrazolo[4,3-f]quinoline hydrochloride melting above 260° C.

Analysis Calculated: C, 52.08; H, 6.99; N, 12.15; Cl, 10.25; S, 18.54, Found: C, 52.21; H, 7.09; N, 12.16; Cl, 10.30; S, 18.39.

A desulfurization mixture was prepared from 0.63 g. of the above compound, one TSP of Raney Ni and 50 ml. of anhydrous ethanol. The mixture was refluxed with stirring for about 3 hours and was then filtered. Evaporation of the solvent in vacuo yielded an oily solid. Water and aqueous ammonium hydroxide were added and the basic mixture extracted several times with equal volumes of methylenedichloride. These extracts were combined, washed with saturated aqueous sodium chloride and then dried. Chromatography of the residue obtained by evaporation of the solvent over florisil with 2-4% MeOH in $CHCl_3$ as the eluant yielded 130 mg. of trans-(±)-6-n-propyl-4,5,5a,6,7,8,9,9a-octahydro-2H(and 3H)-pyrazolo[4,3-f]quinoline. Conversion to the dihydrochloride salt (as above) gave 50 mg. of crystalline product melting above 250° C. after recrystallization from methanol/ethyl acetate; molecular ion, 219 by mass spectrograph.

Analysis Calculated: C, 53.43; H, 7.93; N, 14,38, Found: C, 53.54; H, 8.11; N, 14.45.

Following the above procedure, trans-(±)[or trans-(−)]-1-n-propyl-6-oxo-7-spiro-1′,3′-dithiolanodecahydroquinoline can be reacted with 0.5M lithium diisopropylamine (LDA) reagent in tetrahydrofuran/hexane solvent mixture. The 5-acyl-6-oxo-7-spiro-1′,3′-thiolanodecahydroquinoline thus produced can be cyclized with hydrazine to yield a pyrazole derivative (of Example 1 or Example 2) containing a spirodithioketal at 7. The thioketal group can then be removed according to the above procedure to give trans-(±)[or trans-(−)]-1-$C_1$-$C_3$ alkyl-6-n-propyl-4,5,5a,6,7,8,9,9a-octahydro-2H(and 3H)-pyrazolo[4,3-f]quinoline The (Ts-S-$CH_2$)$_2$ is prepared by the procedure of Organic Synthesis, 54, 33, 37, and 39 (1974).

In the above example, there are several preparations of compounds of formula XXII and XXIII when $R^1$ is methyl, ethyl or n-propyl. We have also developed procedures for the preparation of intermediates wherein $R^1$ can also be $C_{1-3}$ alkyloxy. These latter intermediates can be represented by formulas XXXVII and XXXVIII below and are included within the scope of this invention.

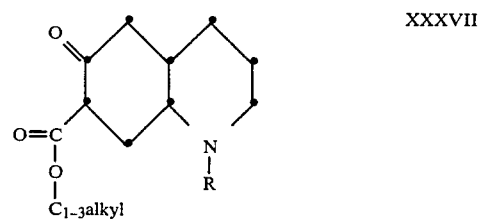

XXXVII

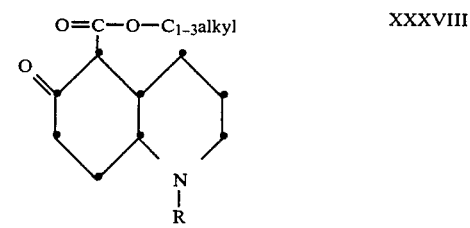

XXXVIII wherein R has its previous meaning. The following examples illustrate the preparation of such compounds.

EXAMPLE 5

Preparation of Intermediates

A suspension of 790 mg. of sodium hydride (55% in mineral oil) was placed in a 50 ml. round bottom flask and the mineral oil removed by three hexane washes. The solid residual sodium hydride was suspended in 8 ml. of THF and 1.45 ml. (1.41 g.) of diethyl carbonate added along with one drop of anhydrous ethanol. The resulting solution was heated to refluxing temperature and 1.1 g. of trans-(±)-1-n-propyl-6-oxodecahydroquinoline in 5 ml. of THF was added over a five minute period. The resulting mixture was heated to reflux temperature overnight. TLC at this point indicated no remaining starting material and a new, slower moving spot was present. The reaction mixture was poured into water giving a pH of the aqueous layer of about 14. The alkaline layer was extracted with methylenedichloride. The pH of the aqueous layer was adjusted to about pH=9 and again the alkaline layer was extracted with methylenedichloride. The methylene dichloride extracts were combined and the combined extracts dried and the solvent removed therefrom to yield 1.56 g. of a yellow oil comprising trans-(±)-1-n-propyl-6-oxo-7-ethoxycarbonyldecahydroquinoline formed in the above reaction. Chromatography of the residue over Woelm silica (100–200 mesh) using a 1:1 ether/hexane solvent mixture containing a trace of 14N aqueous ammonium hydroxide as the eluant. Fractions containing the desired product were combined to yield eventually 880 mg. (55% yield) of a yellow oil. The keto ester was shown by nmr to exist in an enol form represented by the following structure.

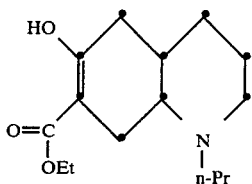

The compound had the following nmr spectrum:
nmr (CDCl$_3$): 12.20 (s, 1H); 4.28 (q, J=7, 2H); 3.20–1.10 (m, 16H); 1.36 (t, J=7, 3H); 0.95 (t, J=7, 3H)

Reaction of the above product with guanidine, for example, yields a trans-(±)-2-amino-4-hydroxy-6-n-propyl-5,5a,6,7,8,9,9a,10-octahydropyrimido[3,4-g]quinoline as set forth in the copending application of Nichols and Kornfeld, Ser. No. 535,503, filed this even day.

While all of the above examples have delineated the preparation of compounds starting with a trans-(±)-bicyclic decahydroquinolinone, it will be apparent to those skilled in the art that identical chemistry would be involved in transforming a trans-(−)-isomer into the corresponding optically active trans-(−) stereoisomeric products and that the trans-(+) tautomers can be prepared in similar fashion.

The compounds of this invention, tautomeric pairs X–XI, XII–XIII, and XVIII–XIX and when R is C$_1$–C$_3$ alkyl or allyl and R$^1$ is H, CH$_3$, C$_2$H$_5$ or n-propyl, reduce the blood pressure of spontaneously hypertensive rats, as illuminated by the following experiment:

Adult male spontaneously hypertensive rats (SHR) (Taconic Farms, Germantown, N.Y.), weighing approximately 300 g. were anesthetized with pentobarbital sodium (60 mg./kg., i.p.). The trachea was cannulated and the SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation. Drugs were administered at a 1 mg./kg. level.

Table 1 which follows gives the results of this test for a series of compounds of this invention. In Table 1, column 1 gives the name of the compound, column 2 the change in mean arterial blood pressure, and column 3, the percent change in cardiac rate.

| Name of Compound | % Change in Mean Arterial Pressure | % Change in Heart Rate |
|---|---|---|
| trans-(±)-3-methyl-5-n-propyl-4,4a,5,6,7,8,8a,9-octahydro-1H(and 2H)pyrazolo[3,4-g]quinoline diHCl | −27 | −27 |
| trans-(±)-3-ethyl-5-n-propyl-4,4a,5,6,7,8,8a,9-octahydro-1H(and 2H)pyrazolo[3,4-g]quionoline diHCl | −32 | −32 |
| trans-(±)-3,5-di-n-propyl-4,4a,5,6,7,8,8a,9-octahydro-1H(and 2H)—pyrazolo[3,4-g]quinoline diHCl | −20 | −9 |
| trans-(±)-1-methyl-6-n-propyl-4,5,5a,6,7,8,9,9a-octahydro-2H(and 3H)—pyrazolo[4,3-f]quinoline diHCl | −30 | 0 |
| trans-(±)-1-ethyl-6-n-propyl-4,5,5a,6,7,8,9,9a-octahydro-2H(and 3H)—pyrazolo[4,3-f]quinoline diHCl | −29 | −9 |
| trans-(±)-1,6-di-n-propyl-4,5,5a,6,7,8,9,9a-octahydro-2H(and 3H)pyrazolo[4,3-f]quinoline diHCl | −30 | −38 |

The compounds of this invention can be administered for therapeutic purposes in a variety of formulations as illustrated below.

Hard gelatin capsules are prepared using the following ingredients:

| | Quantity (Mg./Capsule) |
|---|---|
| Active compound | 50–100 mg. |
| Starch dried | 200 |
| Magnesium stearate | 10 |

The above ingredients are mixed and filled into hard gelatin capsules.

A tablet formulation is prepared using the ingredients below:

| | Quantity (Mg./Tablet) |
|---|---|
| Active compound | 50–100 mg. |
| Cellulose, microcrystalline | 400 |
| Silicon dioxide, fumed | 10 |
| Stearic acid | 5 |

The components are blended and compressed to form tablets.

Alternatively, tablets each containing 50–100 mg. of active ingredient are made up as follows:

| | |
|---|---|
| Active ingredient | 50–100 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 80 mg. of medicament are made as follows:

| Active ingredient | 50-100 mg. |
| --- | --- |
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 50-100 mg. of medicament per 5 ml. dose are made as follows:

| Active ingredient | 50-100 mg. |
| --- | --- |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

For oral administration, tablets, capsules or suspensions containing from about 50 to about 100 mg. of active drug per dose are given 3-4 times a day, giving a daily dosage of 150 to 400 mgs.

We claim:

1. A trans-(±)-tautomeric mixture of the formulas

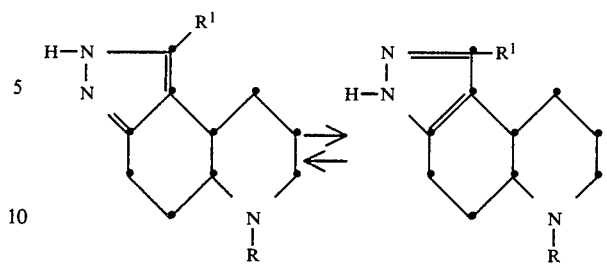

wherein R is H, CN, $C_1$-$C_3$ alkyl or allyl, $R^1$ is methyl, ethyl, or n-propyl or a pharmaceutically-acceptable acid addition salt thereof.

2. A tautomeric mixture according to claim 1 in which R is $C_1$-$C_3$ alkyl or allyl.

3. A tautomeric mixture according to claim 1 in which R is H or CN.

4. A dihydrohalide salt of compound according to claim 1.

5. A dihydrochloride salt of a compound according to claim 1.

6. A compound according to claim 1, said compound being trans-(±)-1-methyl-6-n-propyl-4,5,5a,6,7,8,9,9a-octahydro-2H(and 3H)pyrazolo[4,3-f]quinoline dihydrochloride.

7. A trans-(±)-tautomeric mixture of the formulas

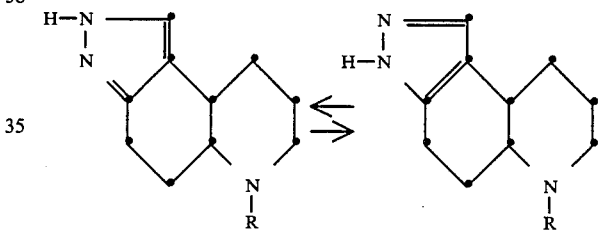

wherein R is H, CN, $C_1$-$C_3$ alkyl or allyl.

8. A tautomeric mixture according to claim 7 in which R is $C_1$-$C_3$ alkyl or allyl.

* * * * *